(12) United States Patent
Zhang et al.

(10) Patent No.: US 9,168,509 B2
(45) Date of Patent: Oct. 27, 2015

(54) HYDROGENATION CATALYSTS AND THE PREPARATION PROCESSES THEREOF

(71) Applicants: CHINA PETROLEUM & CHEMCIAL CORPORATION, Beijing (CN); FUSHUN RESEARCH INSTITUTE OF PETROLEUM AND PETROCHEMICALS, SINOPEC, Fushun, Liaoning Province (CN)

(72) Inventors: Yanxia Zhang, Fushun (CN); Shenghua Yuan, Fushun (CN); Peng Gao, Fushun (CN); Hao Zhang, Fushun (CN); Qiuhong Fu, Fushun (CN); Ri Duan, Fushun (CN)

(73) Assignees: China Petroleum & Chemical Corp., Beijing (CN); Fushun Research Institute of Petroleum, Fushun, Liaoning Province (CN)

( * ) Notice: Subject to any disclaimer, the term of this patent is extended or adjusted under 35 U.S.C. 154(b) by 224 days.

(21) Appl. No.: 13/663,733

(22) Filed: Oct. 30, 2012

(65) Prior Publication Data

US 2013/0123549 A1 May 16, 2013

(30) Foreign Application Priority Data

Nov. 9, 2011 (CN) .......................... 2011 1 0350785
Nov. 9, 2011 (CN) .......................... 2011 1 0350798

(51) Int. Cl.

| | | |
|---|---|---|
| *B01J 23/00* | (2006.01) | |
| *B01J 23/10* | (2006.01) | |
| *B01J 23/70* | (2006.01) | |
| *B01J 23/72* | (2006.01) | |
| *B01J 23/76* | (2006.01) | |
| *B01J 23/80* | (2006.01) | |
| *C07C 27/04* | (2006.01) | |
| *C07C 29/149* | (2006.01) | |
| *B01J 23/83* | (2006.01) | |
| *B01J 23/885* | (2006.01) | |
| *B01J 23/888* | (2006.01) | |
| *B01J 37/03* | (2006.01) | |
| *B01J 23/889* | (2006.01) | |
| *B01J 23/887* | (2006.01) | |
| *B01J 35/02* | (2006.01) | |
| *B01J 35/10* | (2006.01) | |
| *B01J 37/00* | (2006.01) | |

(52) U.S. Cl.
CPC ................ *B01J 23/80* (2013.01); *B01J 23/002* (2013.01); *B01J 23/83* (2013.01); *B01J 23/885* (2013.01); *B01J 23/888* (2013.01); *B01J 23/8871* (2013.01); *B01J 23/8872* (2013.01); *B01J 23/8873* (2013.01); *B01J 23/8892* (2013.01); *B01J 35/023* (2013.01); *B01J 35/1014* (2013.01); *B01J 35/1038* (2013.01); *B01J 35/1061* (2013.01); *B01J 37/0009* (2013.01); *B01J 37/0018* (2013.01); *B01J 37/031* (2013.01); *C07C 29/149* (2013.01); *B01J 2523/00* (2013.01)

(58) Field of Classification Search
CPC ............ B01J 23/70; B01J 23/72; B01J 23/76; B01J 23/80; B01J 23/00; B01J 23/10; C07C 27/04; C07C 29/149; C07C 31/207
USPC ......... 502/304, 306–309, 318, 322–324, 346; 568/700, 864
See application file for complete search history.

(56) References Cited

U.S. PATENT DOCUMENTS

| | | | | |
|---|---|---|---|---|
| 5,124,295 | A * | 6/1992 | Nebesh et al. .................. | 502/64 |
| 5,134,108 | A * | 7/1992 | Thakur et al. .................. | 502/318 |
| 5,142,067 | A * | 8/1992 | Wegman et al. ............... | 549/326 |
| 5,386,066 | A * | 1/1995 | Schneider et al. ............. | 568/885 |
| 5,406,004 | A * | 4/1995 | Eastland et al. ............... | 568/831 |
| 5,453,412 | A * | 9/1995 | Deckers et al. ................ | 502/342 |
| 5,977,417 | A | 11/1999 | Fischer et al. | |
| 5,990,040 | A * | 11/1999 | Hu et al. ........................ | 502/342 |
| 6,787,677 | B2 * | 9/2004 | Maas et al. ..................... | 568/862 |
| 7,119,237 | B2 * | 10/2006 | Prinz et al. ..................... | 568/885 |
| 7,749,376 | B2 * | 7/2010 | Turbevillle et al. ........... | 208/246 |
| 8,680,350 | B2 * | 3/2014 | Hatscher et al. ............... | 585/262 |
| 8,841,232 | B1 * | 9/2014 | Borduz et al. ................. | 502/300 |

FOREIGN PATENT DOCUMENTS

| | | |
|---|---|---|
| CN | 1116616 A | 2/1996 |
| CN | 1137944 A | 12/1996 |
| CN | 1182639 A | 5/1998 |
| CN | 1182732 A | 5/1998 |

(Continued)

OTHER PUBLICATIONS

Yin, A., et al, "Synthesis of Efficient Cu/Al-HMS Catalytic Material and Its Application in Catalytic Hydrogenation of Dimethyl Oxalate," Journal of Shanghai Normal University (Natural Sciences), pp. 40-41 (Nov. 2009).

*Primary Examiner* — Patricia L Hailey
(74) *Attorney, Agent, or Firm* — Finnegan, Henderson, Farabow, Garrett & Dunner LLP

(57) ABSTRACT

The present disclosure provides a hydrogenation catalyst, the preparation process thereof and the application thereof in the production of 1,4-butanediol by hydrogenating dialkyl maleate and/or dialkyl succinate. The catalyst comprises Cu—Al-A-B—O, wherein A comprises at least one of Zn, Mo and W, B comprises at least one of Ba, Mn, Mg, Ti, Ce and Zr. In the process for preparing said hydrogenation catalyst, a part of Cu and A are precipitated first and the rest of Cu, Al and B are precipitated successively.

25 Claims, No Drawings

(56) References Cited

FOREIGN PATENT DOCUMENTS

| | | |
|---|---|---|
| CN | 1286142 A | 3/2001 |
| CN | 1493569 A | 5/2004 |
| CN | 1935375 A | 3/2007 |
| CN | 101307042 A | 11/2008 |
| CN | 101422732 A | 5/2009 |
| CN | 101502803 A | 8/2009 |
| CN | 101891592 A | 11/2010 |
| EP | 0143634 A2 | 6/1935 |
| EP | 0434062 B1 | 6/1994 |
| EP | 0700886 B1 | 3/1996 |
| WO | 2008/009568 * | 1/2008 ............... B01J 23/80 |

* cited by examiner

HYDROGENATION CATALYSTS AND THE PREPARATION PROCESSES THEREOF

The present disclosure relates to a hydrogenation catalyst and the preparation process thereof, especially the hydrogenation catalyst used in production of 1,4-butanediol and coproduction of tetrahydrofuran and γ-butyrolactone by the gas phase hydrogenation using dialkyl maleate and/or dialkyl succinate as the raw materials and the preparation process thereof.

1,4-butanediol is an important basic organic chemical material and is mainly used to produce tetrahydrofuran, polybutylene terephthalate (PBT), γ-butyrolactone and polyurethane (PU). In recent years, with the rapidly increasing demand for thermoplastic elastic fiber and elastomer, the demand for PTMEG (polytetramethylene ether glycol) and PTMG (polytetramethylene glycol) as monomers is strong, so that the demand for the upstream raw material 1,4-butanediol increases rapidly. The major manufacturers of 1,4-butanediol in the world such as BASF and DUPON enlarge their production capacities one after another. Tetrahydrofuran is an excellent solvent and an important organic chemical material, and the biggest use thereof is that it can produce PTMG through polycondensation with 1,4-butanediol and can produce PTMEG through self-polycondensation, γ-butyrolactone is an important organic chemical material and line chemical intermediate, and it is also a high boiling solvent with good properties, strong solubility, good electrical property and high stability, which is non-toxic and safe to use. The most important use of γ-butyrolactone is to produce methyl pyrrolidone.

Currently, there are five main industrialized production, routes for 1,4-butanediol: 1. Reppe process using acetylene and formaldehyde as raw materials; 2. the hydrogenation process using maleic anhydride as raw materials; 3. the gas phase hydrogenation process of dialkyl maleate; 4. the synthesis process using propylene as raw material; and 5. the synthesis process using butadiene as raw material. Currently, the most widely used process is Reppe process, but the gas phase hydrogenation process of dialkyl maleate attracts more and more attention because the boiling point of the raw material is relatively low and this process can use the relatively mature fixed-bed reaction unit.

But in the prior art, the catalyst is easy to be poisoned and broken up. The main reason is that dialkyl succinate reacts with the water generated in the reaction and produces succinic acid. The succinic acid adheres to the surface of the catalyst strongly or reacts with the catalyst, which makes the catalyst to be poisoned or pulverized, and finally makes the conversion rate of raw material to be reduced, or the pressure drop of the bed of the reactor to he increased and the power consumption to be increased.

CN1182732A discloses $CuO-Cr_2O_3-Al_2O_3$ catalyst, which is prepared according to the following process: dissolving the metal salt hi deionized water, stirring it well and then adding ammonia liquor until the pH is 5.0, then filtering, washing, collecting the precipitate, and drying, calcining the precipitate. This process has the problem of the treatment of waste water and is not friendly to environment.

CN1935375A relates to a new catalyst for preparing 1,4-butanediol by the hydrogenation of dimethyl maleate. Said catalyst is prepared using mesoporous molecular sieve MCM-41 as support and impregnating it with the solution of Cu salt to prepare catalyst, precursor, then the precursor is calcined so as to obtain the Cu/MCM-41 catalyst. Since the impregnation method can load a limited amount of metal, the activity and conversion rate of the catalyst are not very high.

EP0143634 discloses a process for the production of 1,4-butanediol and the coproduction of tetrahydrofuran and γ-butyrolactone by gas phase hydrogenation of diethyl maleate and/or butane diacid diethyl ester, wherein the catalyst used therein is the one containing Cu—Cr. CN1116616A discloses a production process of 1,4-butanediol by the gas phase hydrogenation using dialkyl maleate and/or dialkyl succinate as raw materials, wherein the general formula of the catalyst used therein is $Cu_aZnCr_bM_cO_x$ (M is an element selected from IVB group, especially element Zr). CN1137944A uses $CuCr_aMn_bBa_cM_dO_x$(M=Al or Ti) and CN1182639A uses $CuCr_aZn_bTi_cO_x$ to hydrogenate maleic anhydride and/or the esters thereof in order to produce 1,4-butanediol. The aforesaid catalysts are the ones containing chromium oxide, although they have relatively high catalytic activity and good selectivity, the production and recovery of this kind of catalysts will cause serious pollution to the environment.

CN101422732A discloses a catalyst for preparing 1,4-butanediol by the hydrogenation of diethyl succinate and the preparation process thereof. Based on the total weight of the catalyst, copper oxide makes up 30%~60%, zinc oxide makes up 20%~50%, and titanium oxide makes up 5%~20%. When preparing the catalyst, the soluble salts of copper, zinc and titanium are formulated into a metal ion mixed solution, drop wise adding metal ion mixed solution and precipitator simultaneously under stirring and being heated in water bath, controlling the pH of the solution to be 7~8, and then carrying out the aging, filtering, washing, drying and calcining to produce the catalyst. The selectivity of the catalyst prepared by this process need to be further improved, and conversion of the catalyst is relatively low.

CN 1493569A discloses a process for preparing γ-butyrolactone and/or 1,4-butanediol by use of Cr-free type catalyst. The catalyst used in this process is Cu—Mn—Al catalyst, and the preparation process thereof is as follow: dissolving Cu—Mn—Al soluble salt into deionized water, precipitating the solution with base at the temperature of 20~50° C. until pH is 5~8, and then carrying out the aging, filtering, washing and calcining to produce the catalyst. The catalyst prepared by this process has high total amount of acid sites and good initial activity, but has poor stability. After 500 hours' evaluation, the strength of the catalysts will reduce, and a part of catalysts will have the phenomenon of pulverization.

CN101502803A discloses a catalyst for preparing 1,4-butanediol or tetrahydrofuran by selective hydrogenation of dimethyl maleate and the preparation process thereof. The catalyst has a composition of Cu—Zn—Al-M-O, and the molar content of each metal element is as follows: 30 to 60 percent of Cu, 10 to 50 percent of Zn, 5 to 20 percent of Al and 0to 10 percent of M, wherein M is any one of Mn, Mg and Cr. The preparation process of the catalyst is as follows: simultaneously dropwise adding the mixed solution of the soluble salts of Cu, Zn and M and the precipitator for co-precipitation, wherein the pH value is 6.8~7.2, to obtain Cu—Zn-M-O precipitate, then adding aluminum hydroxide and water under stirring, and drying, calcining, granulating to obtain the catalyst. The amount of acid sites of the catalyst prepared by this process is high, so that the selectivity of the catalyst is relatively low and the stability is poor. During the reaction process, the activity of the catalyst is affected greatly by temperature and pressure, and the quality of the product will be affected even by the slight fluctuation of temperature and pressure.

To overcome at least one of the defects existed in the prior art, the present disclosure provides a hydrogenation catalyst and the preparation process thereof. This process has the following advantages: it is simple and is friendly to environment; during the production of 1,4-butanediol by hydrogenating dialkyl maleate and/or dialkyl succinate, the catalyst has high activity and good stability; the pressure drop of the reactor bed is not increased significantly; it is suitable for the process for producing 1,4-butanediol and for coproducing tetrahydrofuran and γ-butyrolactone.

The present disclosure provides a hydrogenation catalyst comprising Cu—Al-A-B—O, wherein A comprises at least one of Zn, Mo and W, B comprises at least one of Ba, Mn, Mg, Ti, Ce and Zr; based on the weight of the catalyst, the content of copper oxide is about 30%~70%, such as about 30%~65%, the content of aluminum oxide is about 10%~40%, the content of A calculated as oxide is about 20%~50%, the content of B calculated as oxide is about 5%~15%; the acid distribution measured by the ammonia adsorption-TPD method is as follows; the amount of acid sites at the temperature of 150~250° C. is about 0.025~0.070 mmol/g, the amount of acid sites at the temperature of 250~400° C. is about 0.020~0.065 mmol/g, the amount of acid sites at the temperature of 400~500° C. is about 0.005~0.020 mmol/g.

In the present disclosure, the ammonia adsorption-TPD method is determined according to ASTM D4824-2003.

In some embodiments of the present disclosure, A comprises at least one of Zn, Mo and W, such as Zn and/or Mo, B comprises at least one of Ba, Mn, Mg, Ti, Ce and Zr, such as at least one of Mn, Zr and Ti.

In the hydrogenation catalyst, the total content of soluble reactive metal ion of copper and aluminum, calculated as the oxide, is about 0.5%~4.0% of the weight of the catalyst.

In certain embodiments, the process for preparing a hydrogenation catalyst comprising:

(1) preparing a first mixed solution comprising soluble salts of Cu and A, wherein A comprises at least one of Zn, Mo and W; and simultaneously dropwise adding the first mixed solution and a precipitator I under stirring to form a precipitation system, wherein the pH value of the precipitation system ranges from about 4.0 to about 6.5, the temperature of the precipitation system ranges from about 15° C. to about 40"C.; wherein the amount of Cu used in step (1) is about 45 wt %~55 wt % of the total used amount of Cu, and the rest of Cu will be introduced in step (2);

(2) preparing a second mixed solution comprising Cu, Al and B, wherein B comprises at least one of Ba, Mn, Mg, Ti, Ce and Zr; and simultaneously dropwise adding the second mixed solution and a precipitator II to the precipitation system obtained in step (1) under stirring, wherein the temperature of the precipitation system ranges from about 45° C. to about 80° C., and the pH value of the precipitation system ranges from about 5.5 to about 8.5;

(3) drying the precipitation system obtained in step (2) at a temperature ranging from about 100° C. to about 200° C., and then calcining for a period of time ranging from about 2 hours to about 8 hours at a temperature ranging from about 500° C. to about 900° C. to obtain the hydrogenation catalyst.

In some embodiments of the present disclosure, the preparation process of the hydrogenation catalyst provided herein includes:

(1) preparing a first mixed solution comprising soluble salts of Cu and A; and simultaneously drop wise adding the first mixed solution of the soluble salts of Cu and A and a precipitator 1 under stirring to form a precipitation system, wherein the pH value of the precipitation system is about 4.0~6.5, the temperature of the system is about 15~40° C.; stirring the system at constant temperature for about 30~90 minutes after the dropwise adding ends, wherein the amount of Cu used in step (1) is about 45 wt %~55 wt % of the total used amount of Cu, and the rest of Cu will be introduced in step (2);

(2) preparing a second mixed solution comprising soluble salts of Cu, Al and B; and simultaneously drop wise adding the second mixed solution of the soluble salts of Cu, Al and B and the precipitator II into the precipitation system obtained in step (1) under stirring, meanwhile, increasing the temperature of the system to about 45~80° C., controlling the pH value of the precipitation system to be about 5.5~8.5, stirring the system at constant temperature for about 80~120 minutes after the dropwise adding ends;

(3) drying the product obtained in step (2) at the temperature of about 100~200° C., and then calcining it for about 2~8 hours at the temperature of about 500~900° C., such as about 600~850° C., to obtain the catalyst.

In one embodiment of the present disclosure, in the step (1) of the process of the present disclosure, the total concentration of metal ions of Cu and A is controlled to be about 0.5~3.5 mol/l, such as about 0.8~3.0 mol/l; and the concentration of the precipitator is about 3.0~6.0 mol/l.

In one embodiment of the present disclosure, in the step (2) of the process of the present disclosure, the total concentration of metal ions of Cu, Al and B is controlled to be about 0.5~3.5 mol/l, such as about 0.8~2.0 mol/l; and the concentration of the precipitator is about 1.0~2.0 mol/l.

In some embodiments of the present disclosure, said soluble salts of Co, Al, A and B can be one or more of nitrate and acetate thereof. For instance, when A is W, the soluble salt thereof may be ammonium metatungstate. The precipitator may comprise at least one of ammonium bicarbonate, ammonium carbonate and ammonia, liquor. In one embodiment, all the raw materials used do not contain heteroion such as $Na^+$, $Cl^-$ or $SO_4^{2-}$.

In some embodiments, in step (3), the drying temperature ranging from about 100° C. to about 200° C. is obtained at the heating rate of about 6° C.~10° C./min, such as 10° C./min In some embodiments of the present disclosure, polyether type nomonic surfactant may be added in step (2) of the present disclosure, and the added amount of the polyether type nonionic surfactant is about 0.05%~2.0% of the volume of the materials obtained in step (2).

In some embodiments of the present disclosure, the polyether type nonionic surfactant can be added directly to the mixed solution of the soluble salts of Cu, Al and B, can be added to the precipitator, or can be added to the reaction system. Said polyether type nonionic surfactant may comprise, for instance, at least one of RPE-type nonionic surfactants and PEP-type nonionic surfactants, for example, at least, one of polyoxyethylene polyoxypropylene penterythritol ether, polyoxyethylene polyoxypropylene ether, polyoxypropylene glycerol ether and polyoxypropylene oxyethylene glycerol ether. This polyether type nonionic surfactant has relatively large molecular weight and good defoaming effect, can make the pore size distribution of the catalyst to be more concentrated while not introducing the heteroions such as $Na^+$, $Ca^{2+}$, $K^+$, $Cl^-$, $Br^-$, $F^-$ and $I^-$ and thus improves the reaction activity of the catalyst.

In some embodiments of the present disclosure, the hydrogenation catalyst prepared according to the process of the present disclosure may have the following properties: the specific surface area is about 25~50 m²/g, the pore volume is about 0.10~0.25 ml/g, average pore diameter is about 14~25 nm, pore size distribution: the volume of the pores with diameter of about 10~30 nm makes up about 75%~95%, such as about 80%~95%, of the total pore volume.

In some embodiments of the present disclosure, the specific surface area of the catalyst and the parameters of pore structure may be measured by low temperature liquid nitrogen adsorption method and by ASAP2420 low temperature liquid, nitrogen, physical adsorption instrument from Micromeritics Instrument of U.S.A.

The present disclosure provides a catalyst comprising a composition of Cu—Al-A-B—O, which does not have the loss of metal ions so as to avoid environmental pollution. There is no need to wash or filter the reaction product so that a large amount of water will be saved. The present disclosure uses the precipitations carried out in two steps under different conditions, i.e. the first step of precipitation of a part of Cu and A and the second step of precipitation of the rest of Cu, Al and B, The second step of the precipitation of the rest of Cu, Al. and B is carried out on the basis of the first step of precipitation, which will help the catalyst to form a stable skeleton structure. Thus it is not easy to collapse during the reaction process. Moreover, the catalyst will have suitable acid content and acid distribution, which improves the reaction activity, selectivity and stability of the catalyst.

The use of said catalyst in the hydrogenation reaction of dialkyl maleate and/or dialkyl succinate can produce with high selectivity 1,4-butanediol and coproduce tetrahydrofuran and γ-butyrolactone. The catalyst has high activity, good selectivity and good stability. In the process of the present disclosure, the alkyl of said dialkyl maleate and/or dialkyl succinate may be chosen from C1~C4 alkyls, such as dimethyl maleate and/or dimethyl succinate, diethyl maleate and/or diethyl succinate, dibutyl maleate and/or dibutyl succinate.

The following non-limiting Examples will be provided to further describe the preparation of the catalyst used for producing 1,4-butanediol and coproducing tetrahydrofuran and γ-butyrolactone. In the present disclosure, wt % refers to weight fraction.

In the present disclosure, the soluble ions are measured as follows: stirring 100 ml acetic acid (with the concentration of 10 wt %) and 10 g catalyst powder at room temperature for 1 hour, then separating the solution, filtering and washing, quantitatively analyze the ion content in the solution by using inorganic method.

The activity of the catalyst provided by the present disclosure can be evaluated by the following method:

The activity of catalyst is evaluated in fixed-bed micro-reactor. The catalyst powder is pressed into the tablets of 40~60 mesh, which are loaded into the reaction tube (with the inner diameter of 15 mm) of the micro-reactor, and the reduction activation of the catalyst is earned out with diluted $H_2$. The raw materials dialkyl maleate and/or dialkyl succinate are used as reaction solution and are pumped into the reaction tube through a constant-flux pump, then increase the pressure and the temperature to carry out reaction. The reaction pressure is 4~8 MPa, such as 5~6 MPa, the reaction temperature is 160~240° C., such as 180~200° C. Hydrogen/ester molar ratio is 100:1~400:1, such as 200:1~300:1 the liquid hourly space velocity of dialkyl maleate and/or dialkyl succinate is 0.1~2.0 $h^{-1}$, such as 0.2~0.5 $h^{-1}$, and the specific Processing Conditions can be selected according to the properties of the raw materials and the requirements on the product and on the basis of the knowledge in the art.

In some embodiments of the present disclosure, the reaction process is as follows: vaporizing the liquid dialkyl maleate and/or dialkyl succinate in proportion under hot hydrogen stream to form vapor mixture with a temperature higher than the dew-point temperature of the raw materials, and then feeding the vapor mixture into the reactor charged with the hydrogenation catalyst.

EXAMPLE 1

(1) At the temperature of 20° C. 1000 ml mixed solution containing 125 g $Cu(NO_3O_2.3H_2O$ and 313.2 g $Zn(NO_3)_2.6H_2O$, and the precipitator ammonia liquor (with the molar concentration of 4.41 mol/l) were dropwise added simultaneously for co-precipitation under stirring, and the pH value of the precipitation system was kept at 5.4; stirred the system at constant temperature for 50 minutes after the dropwise adding ended;

(2) 1000 ml mixed solution of the soluble salts 131.7 g $Cu(NO_3)_2.3H_2O$, 204.4 g $Al(NO_3)_3.9H_2O$ and 48.5 g $Mn(NO_2)_2$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 50° C., and the pH value of the precipitation system was kept at 6.6; stirred the system at constant temperature for 100 minutes after the dropwise adding ended;

(3) the product obtained in step (2) was dried out rapidly at the temperature of 200° C., then it was calcined at the temperature of 700° C. for 4 hours, then the obtained catalyst was pressed and molded to tablets of about 50 mesh, and the tablets were loaded into the micro-reactor for the activity evaluation.

EXAMPLE 2

(1) At the temperature of 20° C. 1000 ml mixed solution containing 115 g $Cu(NO_3)_2.3H_2O$ and 182.3 g $Zn(NO_3)_2.6H_2O$ and the precipitator ammonia liquor (with the molar concentration of 4.41 mol/l) were dropwise added simultaneously for co-precipitation under stirring, and the pH value of the precipitation system was kept to be 6.0; stirred the system at constant temperature for 50 minutes after the dropwise adding ended;

(2) 1000 ml mixed solution of the soluble salts of 98.97 g $Cu(NO_3)_2.3H_2O$, 545.0 g $Al(NO_3)_3.9H_2O$ and 46.46 g $Mn(NO_3)_2$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 70° C., and the pH value of the precipitation system was kept at 7.0; stirred the system at normal temperature for 100 minutes alter the dropwise adding ended;

(3) the product obtained in step (2) was dried out rapidly at the temperature of 200° C., then it was calcined for 4 hours at the temperature of 700° C., then the obtained catalyst was pressed and molded to tablets of about 50 mesh, the tablets were loaded into the micro-reactor for the evaluation of activity.

EXAMPLE 3

(1) At the temperature of 30° C., 125 g $Cu(NO_3)_2.3H_2O$ and 11.4.68 g $(NH_4)_6H_2W_{12}O_{40}.45H_2O$ were dissolved in 1000 ml deionized water, then the solution and the precipitator ammonium, carbonate (with the molar concentration of 3.5 mol/l) were dropwise added for co-precipitation under stirring, and the pH value of the precipitation system was kept at 5.0; stirred the system at constant temperature for 60 minutes after the drop wise adding ended;

(2) 1000 ml mixed solution of the soluble salts of 131 g $Cu(NO_3)_2.3H_2O$, 145.44 g $Al(NO_3)_3.9H_2O$ and 38.4 g $Ti(NO_3)_4$ and the precipitator ammonia liquor (with the molar concentration of 1.5 mol/l) were dropwise added simultaneously to the precipitate obtained in step (1) for co-precipitation under stirring, meanwhile, the temperature of the system was increased to 60° C., and the pH value of the precipitation system was kept at 7.0; stirred the system at constant temperature for 90 minutes after the dropwise adding ended;

(3) the product obtained in step (2) was dried out rapidly at the temperature of 180° C., and then was calcined for 7 hours at the temperature of 600° C.; then the obtained catalyst was pressed and molded to tablets of about 60 mesh, and the tablets were loaded into the micro-reactor for the evaluation of activity.

EXAMPLE 4

(1) At the temperature of 40° C., 1000 ml mixed solution containing 155 g $Cu(NO_3)_2.3H_2O$ and 163.7 g $Mo(NO_3)_6.5H_2O$ and the precipitator ammonia liquor (with the molar concentration of 5.0 mol/l) were dropwise added simultaneously for co-precipitation under stirring, and the pH value of the precipitation system was kept at 6.2; stirred, the system at constant temperature for 60 minutes after the dropwise adding ended;

(2) 1000 ml mixed solution of the soluble salts of 170 g $Cu(NO_3)_2.3H_2O$, 187.0 g $Al(NO_3)_3.9H_2O$ and 70.9 g $Zr(NO_3)_4.5H_2O$ and the precipitator ammonium bicarbonate (with the molar concentration of 2.0 mol/l) were dropwise added simultaneously to the precipitate obtained in step (1) for co-precipitation under stirring, meanwhile, the temperature of the system was increased to 70° C., and the pH value of the precipitation system was kept at 7.5; stirred the system at constant temperature for 120 minutes after the dropwise adding ended;

(3) the product obtained in step (2) was dried out rapidly at the temperature of 150° C., then was calcined for 6 hours at the temperature of 650° C., then the obtained catalyst was pressed and molded to tablets of about 40 mesh, and the tablets were loaded into the micro-reactor for the evaluation of activity.

EXAMPLE 5

(1) At the temperature of 20° C. 1000 ml mixed solution containing 185 g $Cu(NO_3)_2.3H_2O$ and 134.1 g $Zn(NO_3)_2.6H_2O$ and the precipitator ammonia liquor (with the molar concentration of 4.4.1 mol/l) were dropwise added simultaneously for co-precipitation under stirring, and the pH value of the precipitation system was kept at 5.4; stirred the system at constant temperature for 50 minutes after the dropwise adding ended;

(2) 1000 ml mixed solution of the soluble salts of 180 g $Cu(NO_3)_2.3H_2O$, 199.9 g $Al(NO_3)_3.9H_2O$ and 32.8 g $Mn(NO_3)_2$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 50° C., and the pH value of the precipitation system was kept at 6.0; stirred the system at constant temperature for 100 minutes after the dropwise adding ended;

(3) the product obtained in step (2) was dried out rapidly at the temperature of 200° C., and then was calcined for 3 hours at the temperature of 800° C.; then the obtained catalyst was pressed and molded to tablets of about 50 mesh, and the tablets were loaded into the micro-reactor for the evaluation of activity.

EXAMPLE 6

(1) At the temperature of 30° C. 1000 ml mixed solution containing 125 g $Cu(NO_3)_2.3H_2O$ and 304.83 g $Zn(NO_3)_2.6H_2O$ and the precipitator ammonia liquor (with the molar concentration of 4.41 mol/l) were dropwise added simultaneously for co-precipitation under stirring, and the pH value of the precipitation system was kept at 6.0; stirred the system at constant temperature for 50 minutes after the dropwise adding ended;

(2) 1000 ml mixed solution of the soluble salts of 131.7 g $Cu(NO_3)_2.3H_2O$, 176.28 g $Al(NO_3)_3.9H_2O$ and 60.71 g $Zr(NO_3)_4.5H_2O$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 60° C., and the pH value of the precipitation system was kept at 7.5; stirred the system at constant temperature for 100 minutes after the dropwise adding ended;

(3) the product obtained in Step (2) was dried out rapidly at the temperature of 200° C., and then was calcined for 3 hours at the temperature of 600° C.; then the obtained catalyst was pressed and molded to tablets of about 50 mesh, and the tablets were loaded into the micro-reactor for the evaluation of activity.

EXAMPLE 7

(1) At the temperature of 20° C., 1000 ml mixed solution containing 148 g $Cu(NO_3)_2.3H_2O$ and 217.79 g $Zn(NO_3)_2.6H_2O$ and the precipitator ammonia liquor (with the molar concentration of 4.41 mol/l) were dropwise added simultaneously for co-precipitation under stirring, and the pH value of the precipitation system was kept at 5.8; stirred the system at constant temperature for 50 minutes after the dropwise adding ended;

(2) 1000 ml mixed solution of the soluble salts of 148.26 g $Cu(NO_3)_2.3H_2O$, 240.44 g $Al(NO_3)_3.9H_2O$ and 75.91 g $Zr(NO_3)_4.5H_2O$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 70° C., and the pH value of the precipitation system was kept at 7.5; stirred the system at constant temperature for 100 minutes after the dropwise adding ended;

(3) the product obtained in step (2) was dried out rapidly at the temperature of 200° C., then was calcined for 3 hours at the temperature of 800° C.; then the obtained catalyst was pressed and molded to tablets of about 50 mesh, and the tablets were loaded into the micro-reactor for the evaluation of activity.

EXAMPLE 8

(1) At the temperature of 20° C., 1000 ml mixed solution containing 105 g $Cu(NO_3)_2.3H_2O$ and 182.34 g $Zn(NO_3)_2.6H_2O$ and the precipitator ammonia liquor (with the molar concentration of 4.4.1 mol/l) were dropwise added simultaneously for co-precipitation under stirring, and the pH value of the precipitation system was kept at 5.4; stirred the system at constant temperature for 50 minutes after the dropwise adding ended;

(2) 1000 ml mixed solution of the soluble salts of 109 g $Cu(NO_3)_2.3H_2O$, 488.90 g $Al(NO_3)_3.9H_2O$, 45.54 g $Zr(NO_3)_4.5H_2O$ and 32.79 g $Mn(NO_3)_2$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 70° C., and the pH value of the precipitation system was kept at 6.0; stirred the system at constant temperature for 100 minutes after the dropwise adding ended;

(3) the product obtained in step (2) was dried out rapidly at the temperature of 200° C., then was calcined for 3 hours at the temperature of 800° C.; then the obtained catalyst was pressed and molded to tablets of about 50 mesh, and the tablets were loaded into the micro-reactor for the evaluation of activity.

EXAMPLE 9

(1) At the temperature of 25° C., 1000 ml mixed solution containing 11.2 g $Cu(NO_3)_2.3H_2O$ and 302.00 g $Zn(NO_3)_2.6H_2O$ and the precipitator ammonia liquor (with the molar concentration of 4.41 mol/l) were dropwise added simultaneously for co-precipitation under stirring, and the phi value of the precipitation system was kept at 5.6; stirred the system at constant temperature for 50 minutes alter the dropwise adding ended;

(2) 1000 ml mixed solution of the soluble salts of 118.43 g $Cu(NO_3)_2.3H_2O$, 238.83 g $Al(NO_3)_3.9H_2O$ and 68.67 g $Ti(NO_3)_4$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 65° C., and the pH value of the precipitation system was kept at 6.5; stirred the system at constant temperature for 100 minutes after the dropwise adding ended;

(3) the product obtained in step (2) was dried out rapidly at the temperature of 200° C. then was calcined for 3 hours at the temperature of 820° C.; then the obtained catalyst was pressed and molded to tablets of about 50 mesh, and the tablets were loaded into the micro-reactor for the evaluation of activity.

EXAMPLE 10

(1) At the temperature of 25° C., 1000 ml mixed solution containing 165 g $Cu(NO_3)_2.3H_2O$ and 166.97 g $Zn(NO_3)_2.6H_2O$ and the precipitator ammonia liquor (with the molar concentration of 4.41 mol/l) were dropwise added simultaneously for co-precipitation under stirring, and the pH value of the precipitation system was kept at 5.6; stirred the system at constant temperature for 50 minutes after the dropwise adding ended;

(2) 1000 ml mixed solution of the soluble salts of 164.18 g $Cu(NO_3)_2.3H_2O$, 224.41 g $Al(NO_3)_3.9H_2O$ and 105.03 g $Ti(NO_3)_4$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 65° C., and the pH value of the precipitation system was kept at 6.0; stirred the system at constant temperature for 100 minutes after the dropwise adding ended;

(3) the product obtained in step (2) was dried out rapidly at the temperature of 200° C., then was calcined for 3 hours at the temperature of 820° C.; then the obtained catalyst was pressed and molded to tablets of about 50 mesh, and the tablets were loaded into the micro-reactor for the evaluation of activity.

EXAMPLE 11

(1) At the temperature of 25° C., 1000 ml mixed solution containing 123 g $Cu(NO_3)_2.3H_2O$ and 337.9 g $Mo(NO_3)_6.5H_2O$ and the precipitator ammonia liquor (with the molar concentration of 4.41 mol/l) were dropwise added simultaneously for co-precipitation under stirring, and the pH value of the precipitation system was kept at 5.4; stirred the system at constant temperature for 50 minutes after the dropwise adding ended;

(2) 1000 ml mixed solution of the soluble salts of 127.18 g $Cu(NO_3)_2.3H_2O$, 208.38 g $Al(NO_3)_3.9H_2O$ and 49.19 g $Mn(NO_3)_2$ and the precipitator ammonium carbonate (with the molar concentration of 1.5 mol/l) were dropwise added simultaneously to the precipitate obtained in step (1) for co-precipitation under stirring, meanwhile, the temperature of the system to was increased to 65° C. and the pH value of the precipitation system was kept at 6.0; stirred the system at constant temperature for 100 minutes after the dropwise adding ended;

(3) the product obtained in step (2) was dried out rapidly at the temperature of 200° C., then was calcined for 3 hours at the temperature of 820° C.; then the obtained catalyst was pressed and molded, to tablets of about 50 mesh, and the tablets were loaded into the micro-reactor for the evaluation of activity.

EXAMPLE 12

(1) At the temperature of 25° C., 1000 ml mixed solution containing 148 g $Cu(NO_3)_2.3H_2O$ and 194.3 g $Mo(NO_3)_6.5H_2O$ and the precipitator ammonia liquor (with the molar concentration of 4.41 mol/l) were dropwise added simultaneously for co-precipitation under stirring, and the pH value of the precipitation system was kept at 5.4; stirred the system at constant temperature for 50 minutes alter the dropwise adding ended;

(2) 1000 ml mixed solution of the soluble salts of 154.85 g $Cu(NO_3)_2.3H_2O$, 320.59 g $Al(NO_3)_3.9H_2O$ and 60.12 g $Mn(NO_3)_2$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 50° C., and the pH value of the precipitation system was kept at 6.0; stirred the system at constant temperature for 100 minutes after the dropwise adding ended;

(3) the product obtained in step (2) was dried out rapidly at the temperature of 200° C., then was calcined for 3 hours at the temperature of 700° C.; then the obtained catalyst was pressed and molded to tablets of about 50 mesh, and the tablets were loaded into the micro-reactor for the evaluation of activity.

EXAMPLE 13

(1) At the temperature of 25° C. 1000 ml mixed solution containing 120 g $Cu(NO_3)_2.3H_2O$ and 363.2 g $Mo(NO_3)_6.5H_2O$ and the precipitator ammonia liquor (with the molar concentration of 4.41 mol/l) were dropwise added simultaneously for co-precipitation under stirring, and the pH value of the precipitation system was kept at 6.0; stirred the system at constant temperature for 50 minutes alter the dropwise adding ended;

(2) 1000 ml mixed solution of the soluble salts of 117.01 g $Cu(NO_3)_2.3H_2O$, 176.32 g $Al(NO_3)_3.9H_2O$ and 80.79 g $Ti(NO_3)_4$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 70° C., and the pH value of the precipitation system was kept at 6.5; stirred the system at constant temperature for 100 minutes after the dropwise adding ended;

(3) the product obtained in step (2) was dried out rapidly at the temperature of 200° C., then was calcined for 3 hours at the temperature of 700° C.; then the obtained catalyst was pressed and molded to tablets of about 50 mesh, and the tablets were loaded Into the micro-reactor for the evaluation of activity.

EXAMPLE 14

(1) At the temperature of 25° C., 1000 ml mixed solution containing 1.65 g $Cu(NO_3)_2.3H_2O$ and 228.0 g $Mo(NO_3)_6.5H_2O$ and the precipitator ammonia liquor (with the molar concentration of 4.41 mol/l) were dropwise added simultaneously for co-precipitation under stirring, and the pH value of the precipitation system was kept at 5.4; stirred the system at constant temperature for 50 minutes after the dropwise adding ended;

(2) 1000 ml mixed solution of the soluble salts of 164.18 g $Cu(NO_3)_2.3H_2O$, 208.38 g $Al(NO_3)_3.9H_2O$ and 80.79 g $Ti(NO_3)_4$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 50° C., and the pH value of the precipitation system was kept at 6.0, and stirred the system at constant temperature for 100 minutes after the dropwise adding ended;

(3) the product obtained in step (2) was dried out rapidly at the temperature of 200° C., then was calcined for 3 hours at the temperature of 780° C.; then the obtained catalyst was pressed and molded to tablets of about 50 mesh, and the tablets were loaded into the micro-reactor for the evaluation of activity.

EXAMPLE 15

(1) At the temperature of 25° C., 1000 ml mixed solution containing 115 g $Cu(NO_3)_2.3H_2O$ and 122.49 g $(NH_4)_6H_2W_{12}O_{40}.45H_2O$ and the precipitator ammonia liquor (with the molar concentration of 4.41 mol/l) were dropwise added simultaneously for co-precipitation under stirring, and the pH value of the precipitation system was kept at 5.8; stirred the system at constant temperature for 50 minutes after the dropwise adding ended;

(2) 1000 ml mixed solution of the soluble salts of 122.01 g $Cu(NO_3)_2.3H_2O$, 288.53 g $Al(NO_3)_3.9H_2O$ and 27.33 g $Mn(NO_3)_2$, 37.95 g $Zr(NO_3)_4.5H_2O$ and the precipitator ammonium carbonate (with the molar concentration of 1.5 mol/l) were dropwise added simultaneously to the precipitate obtained in step (1) for co-precipitation under stirring, meanwhile, the temperature of the system, was increased, to 58° C., and the pH value of the precipitation system was kept at 6.3; stirred the system at constant temperature for 100 minutes after the dropwise adding ended;

(3) the product obtained in step (2) was dried out rapidly at the temperature of 200° C., then was calcined for 3 hours at the temperature of 820° C.; then, the obtained catalyst was pressed and molded to tablets of about 50 mesh, and the tablets were loaded into the micro-reactor for the evaluation of activity.

EXAMPLE 16

(1) At the temperature of 25° C., 1000 ml mixed solution containing 115 g $Cu(NO_3)_2.3H_2O$ and 132.70 g $(NH_4)_6H_2W_{12}O_{40}.45H_2O$ and the precipitator ammonia liquor (with the molar concentration of 4.41 mol/l) were dropwise added, simultaneously for co-precipitation under stirring, and the pH value of the precipitation system was kept at 5.4; stirred the system at constant temperature for 50 minutes after the dropwise adding ended;

(2) 1000 ml mixed solution of the soluble salts of 122.01 g $Cu(NO_3)_2.3H_2O$, 256.47 g $Al(NO_3)_3.9H_2O$ and 33.44 g $Ba(NO_3)_2$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 65° C., and the pH value of the precipitation system was kept at 7.0; stirred the system at constant temperature for 100 minutes after the dropwise adding ended;

(3) the product obtained in step (2) was dried out rapidly at the temperature of 200° C., then was calcined for 3 hours at the temperature of 820° C.; then the obtained catalyst was pressed and molded to tablets of about 50 mesh, and the tablets were loaded into the micro-reactor for the evaluation of activity.

EXAMPLE 17

(1) At the temperature of 35° C., 1000 ml mixed solution containing 115 g $Cu(NO_3)_2.3H_2O$ and 284.44 g $Zn(NO_3)_2.6H_2O$ and the precipitator ammonia liquor (with the molar concentration of 4.41 mol/l) were dropwise added simultaneously for co-precipitation under stirring, and the pH value of the precipitation system was kept at 5.4; stirred the system at constant temperature for 50 minutes after the dropwise adding ended;

(2) 1000 ml mixed solution of the soluble salts of 115.43 g $Cu(NO_3)_2. 3H_2O$, 240.44 g $Al(NO_3)_3.9H_2O$ and 153.71 g $Mg(NO_3)_2.6H_2O$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 60° C., and the pH value of the precipitation system was kept at 6.2; stirred the system at constant temperature for 100 minutes after the dropwise adding ended;

(3) the product obtained in step (2) was dried out rapidly at the temperature of 200° C., then was calcined for 3 hours at the temperature of 800° C.; then the obtained catalyst was pressed and molded to tablets of about 50 mesh, and the tablets were loaded into the micro-reactor for the evaluation of activity.

EXAMPLE 18

(1) At the temperature of 25° C., 1000 ml mixed solution containing 130 g $Cu(NO_3)_2.3H_2O$ and 262.57 g $Zn(NO_3)_2.6H_2O$ and the precipitator ammonia liquor (with the molar concentration of 4.41 mol/l) were dropwise added simultaneously for co-precipitation under stirring, and the pH value of the precipitation system was kept at 5.6; the mixture was stirred at constant temperature for 50 minutes after the dropwise adding ended;

(2) 1000 ml mixed solution of the soluble salts of 133.34 g $Cu(NO_3)_2.3H_2O$, 224.41 g $Al(NO_3)_3.9H_2O$ and 57.69 g $Ce(NO_3)_3.6H_2O$ and the precipitator ammonium carbonate (with the molar concentration of 1.5 mol/l) was dropwise added simultaneously to the precipitate obtained in step (1) for co-precipitation under stirring, meanwhile, the temperature of the system was increased to 65° C., and the pH value of the precipitation system was kept at 7.5; stirred the system at constant temperature for 100 minutes after the dropwise adding ended;

(3) the product obtained in step (2) was dried out rapidly at the temperature of 200° C., then was calcined for 3 hours at the temperature of 600° C.; then the obtained catalyst was pressed and molded to tablets of about 50 mesh, and the tablets were loaded into the micro-reactor for the evaluation of activity.

EXAMPLE 19

(1) At the temperature of 25° C., 1000 ml mixed solution containing 115 g $Cu(NO_3)_2.3H_2O$ and 346.3 g $Mo(NO_3)_6.5H_2O$ and the precipitator ammonia liquor (with the molar concentration of 4.41 mol/l) were dropwise added simultaneously for co-precipitation under stirring, and the pH value of the precipitation system was kept at 5.4; stirred the system at constant temperature for 50 minutes after the dropwise adding ended;

(2) 1000 ml mixed solution of the soluble salts of 122 g $Cu(NO_3)_2.3H_2O$, 224.41 g $Al(NO_3)_3.9H_2O$ and 68.32 g $Zr(NO_3)_4.5H_2O$ and the precipitator ammonium carbonate (with the molar concentration of 1.5 mol/l) were dropwise added simultaneously to the precipitate obtained in step (1) for co-precipitation under stirring, meanwhile, the temperature of the system, was increased to 60° C. and the pH value of the precipitation system was kept at 6.0; stirred the system at constant temperature for 100 minutes after the dropwise adding ended;

(3) the product obtained in step (2) was dried out rapidly at the temperature of 200° C., then was calcined for 3 hours at the temperature of 750° C.; then the obtained catalyst was pressed and molded to tablets of about 50 mesh, and the tablets were loaded into the micro-reactor for the evaluation of activity.

EXAMPLE 20

(1) At the temperature of 25° C., 1000 ml mixed solution containing 155 g $Cu(NO_3)_2.3H_2O$ and 211 g $Mo(NO_3)_6.5H_2O$ and the precipitator ammonia liquor (with the molar concentration of 4.41 mol/l) were dropwise added simultaneously for co-precipitation under stirring, and the pH value of the precipitation system was kept at 5.8; stirred the system at constant temperature for 50 minutes after the dropwise adding ended;

(2) 1000 ml mixed solution of the soluble salts of 161.01 g $Cu(NO_3)_2.3H_2O$, 240.44 g $Al(NO_3)_3.9H_2O$ and 91.09 g $Zr(NO_3)_4.5H_2O$ and the precipitator ammonium carbonate (with the molar concentration of 1.5 mol/l) were dropwise added simultaneously to the precipitate obtained in step (1) for co-precipitation under stirring, meanwhile, the temperature of the system was increased to 70° C., and the pH value of the precipitation system was kept at 6.2; stirred the system at constant temperature for 100 minutes after the dropwise adding ended;

(3) the product obtained in step (2) was dried out rapidly at the temperature of 200° C., then was calcined for 3 hours at the temperature of 750° C.; then the obtained catalyst was pressed and molded to tablets of about 50 mesh, and the tablets were loaded into the micro-reactor for the evaluation of activity.

EXAMPLE 21

(1) At the temperature of 20° C., 1000 ml mixed solution containing 125 g $Cu(NO_3)_2.3H_2O$ and 313.2 g $Zn(NO_3)_2.6H_2O$ and the precipitator ammonia liquor (with the molar concentration of 4.41 mol/l) were dropwise added simultaneously for co-precipitation under stirring, and the pH value of the precipitation system was kept at 5.4; stirred the system at constant temperature for 50 minutes after the dropwise adding ended;

(2) 1000 ml mixed solution of the soluble salts of 131.7 g $Cu(NO_3)_2.3H_2O$, 204.4 g $Al(NO_3)_3 9H_2O$ and 48.5 g $Mn(NO_3)_2$ (wherein 50 ml polyoxyediylene polyoxypropylene pentaerythritol ether was added) and the precipitator ammonium carbonate (with the molar concentration of 1.7 mol/l) were dropwise added simultaneously to the precipitate obtained in step (1) for co-precipitation under stirring, meanwhile, the temperature of the system was increased to 50° C., and the pH value of the precipitation system was kept at 6.6; stirred the system at constant temperature for 100 minutes after the dropwise adding ended;

(3) the product obtained in step (2) was dried out rapidly at the temperature of 200° C., then was calcined for 4 hours at the temperature of 700° C.; then the obtained catalyst was pressed and molded to tablets of about 50 mesh, and the tablets were loaded into the micro-reactor for the evaluation of activity.

EXAMPLE 22

(1) At the temperature of 30° C., 125 g $Cu(NO_3)_2.3H_2O$ and 114.68 g $(NH_4)_6H_2W_{12}O_{40}.45H_2O$ were dissolved in 1000 ml deionized water, then the precipitator ammonium carbonate (with the molar concentration of 5.0 mol/l) was dropwise added simultaneously for co-precipitation under stirring, and the pH value of the precipitation system was kept at 5.0; stirred the system at constant temperature for 60 minutes after the dropwise adding ended;

(2) 1000 ml mixed solution of the soluble salts of 131 g $Cu(NO_3)_2.3H_2O$, 145.44 g $Al(NO_3)_3.9H_2O$ and 38.4 g $Ti(NO_3)_4$ and the precipitator ammonia liquor (with the molar concentration of 1.5 mol/l, wherein containing 30 ml polyoxyethylene polyoxypropylene ether were dropwise added, simultaneously to the precipitate obtained, in step (1) for co-precipitation under stirring, meanwhile, the temperature of the system was increased to 60° C., and the pH value of the precipitation system was kept at 7.0; stirred, the system at constant temperature for 90 minutes after the dropwise adding ended;

(3) the product obtained in step (2) was dried out rapidly at the temperature of 180° C. then was calcined for 7 hours at the temperature of 600° C.; the obtained catalyst was pressed and molded to tablets of about 60 mesh, and the tablets were loaded into the micro-reactor for the evaluation of activity.

EXAMPLE 23

(1) At the temperature of 40° C., 1000 ml mixed solution containing 155 g $Cu(NO_3)_2.3H_2O$ and 161 g $Mo(NO_3)_6 5H_2O$ and the precipitator ammonia liquor (with the molar concentration of 5.0 mol/l) were dropwise added: simultaneously for co-precipitation under stirring, and the pH value of the precipitation system was kept at 6.2; stirred the system at constant temperature for 60 minutes alter the dropwise adding ended;

(2) firstly, 25 ml polyoxypropylene oxyethylene glycerol ether were added to the precipitate obtained in step (1) and were stirred well, and then 1000 ml mixed solution of the soluble salts of 170 g $Cu(NO_3)_2 \cdot 3H_2O$, 187.0 g $Al(NO_3)_3 \cdot 9H_2O$ and 70.9 g $Zr(NO_3)_4 \cdot 5H_2O$ and the precipitator ammonium bicarbonate (with the molar concentration of 2.0 mol/l$^{-1}$) were added simultaneously to the precipitate obtained in step (1) for co-precipitation under stirring, meanwhile, the temperature of the system was increased to 70° C., and the pH value of the precipitation system was kept at 7.5: stirred the system at constant temperature for 120 minutes after die dropwise adding ended;

(3) the product obtained in step (2) was dried out rapidly at the temperature of 150° C., then was calcined for 6 hours at the temperature of 650° C.; the obtained catalyst was pressed and molded to tablets of about 40 mesh, and the tablets were loaded into the micro-reactor for the evaluation, of activity.

EXAMPLE 24

(1) At the temperature of 20° C., 1000 ml mixed solution containing 185 g $Cu(NO_3)_2 \cdot 3H_2O$ and 134.1 g $Zn(NO_3)_2 \cdot 6H_2O$ and the precipitator ammonia liquor (with the molar concentration of 4.41 mol/l) were dropwise added simultaneously for co-precipitation under stirring, and the pH value of the precipitation system was kept at 5.4; stirred the system at constant temperature for 50 minutes after the dropwise adding ended;

(2) 1000 ml mixed solution of the soluble salts of 180 g $Cu(NO_3)_2 3H_2O$, 199.9 g $Al(NO_3)_3 9H_2O$ and 32.8 g $Mn(NO_3)_2$ and the precipitator ammonium carbonate (with the molar concentration, of 1.5 mol/l$^{-1}$) were dropwise added simultaneously to the precipitate obtained in step (1) for co-precipitation under stirring, meanwhile, 15 ml polyoxypropylene glycerol ether was added, the temperature of the system was increased to 50° C., and the pH value of the precipitation system was kept at 6.0; stirred die system at constant temperature for 100 minutes after the dropwise adding ended;

(3) the product obtained in step (2) was dried out rapidly at the temperature of 200° C., then was calcined for 3 hours at the temperature of 800° C.; the obtained catalyst was pressed and molded to tablets of about 50 mesh, and the tablets were loaded into the micro-reactor for the evaluation of activity.

COMPARATIVE EXAMPLE 1

213.97 g $Cu(NO_3)_2 \cdot 3H_2O$, 46.46 g $Mn(NO_3)_2$, 182.3 g $Zn(NO_3)_2 \cdot 6H_2O$ and 545 g $Al(NO_3)_3 \cdot 9H_2O$ were dissolved in 1000 ml deionized water to obtain solution A. The precipitator ammonia liquor (with the molar concentration of 4.41 mol/l) was prepared as solution B, 200 ml deionized water was charged into a 2000 ml beaker. Solutions A and B were added simultaneously into another beaker under stirring, the dripping speeds of solutions A and B were controlled so that the pH value of the solution was kept at 5.5±0.5. Stirring was kept for 1 hour after the titration ended, and then the solution was filtrated, by suction and washed for 6 times, the precipitate was collected and dried for 3 hours at the temperature of 120° C., and was calcined for 2 hours at the temperature of 700° C. to obtain the catalyst; the obtained catalyst was pressed and molded to tablets of about 40 mesh, and the tablets were loaded into the micro-reactor for the evaluation, of activity.

COMPARATIVE EXAMPLE 2

213.97 g $Cu(NO_3)_2 \cdot 3H_2O$, 182.3 g $Zn(NO_3)_2 \cdot 6H_2O$ and 46.46 g $Mn(NO_3)_2$ were dissolved in 1000 ml $H_2O$ to obtain solution of metal ions, and 200 g $Na_2CO_3$ was dissolved in 2000 ml $H_2O$ to obtain precipitator solution. In die water bath of 60° C., the solution of metal ions and the precipitator solution were dropwise added simultaneously under stirring for co-precipitation. The mixture was aged for 1 hour after the dropwise adding ended. The precipitate was washed to remove impurity ions, and then 113.36 g $Al(OH)_3$ was added. 1500 ml deionized water was added to the resulting mixture, then the mixture was heated up to 60° C. and was stirred for 30 minutes. The filter cake obtained by suction filtration was dried overnight at the temperature of 120° C., and then was calcined for 4 hours in a muffle furnace which is heated to the temperature of 700° C. at the heating rate of 10° C./min. The obtained catalyst was pressed and molded to tablets of about 50 mesh, and the tablets were loaded into the micro-reactor for the evaluation of activity.

COMPARATIVE EXAMPLE 3

325 g $Cu(NO_3)_2 \cdot 3H_2O$, 161 g $Mo(NO_3)_6 \cdot 5H_2O$, 70.9 g $Zr(NO_3)_4 \cdot 5H_2O$ and 187 g $Al(NO_3)_3 \cdot 9H_2O$ were dissolved in 1000 ml deionized water to obtain solution A. The precipitator ammonia liquor (with the molar concentration of 4.41 mol/l) was prepared as solution B. 200 ml deionized water was charged into a 2000 ml beaker. Solutions A and B were added simultaneously into another beaker under stirring, the dripping speeds of solutions A and B were controlled, so that the pH value of the solution was kept at 5.5±0.5. Stirred the system for 1 hour after the titration ended, then the solution was filtrated by suction and washed for 6 times, the precipitate was collected, and dried for 3 hours at the temperature of 120° C., and was calcined for 6 hours at the temperature of 650° C. to obtain the catalyst; the obtained catalyst was pressed and molded to tablets of about 40 mesh, and the tablets were loaded into the micro-reactor for the evaluation of activity.

COMPARATIVE EXAMPLE 4

325 g $Cu(NO_3)_2 \cdot 3H_2O$, 161 g $Mo(NO_3)_6 \cdot 5H_2O$, 70.9 g $Zr(NO_3)_4 \cdot 5H_2O$ were dissolved in 1000 ml $H_2O$ to obtain solution of metal, ions, and 200 g $Na_2CO_3$ was dissolved in 2000 ml $H_2O$ to obtain precipitator solution. In the water bath, of 60° C., the solution of metal ions and the precipitator solution were dropwise added simultaneously under stirring for co-precipitation. The mixture was aged for 1 hour alter the dropwise adding ended. The precipitate was washed to remove impurity ions, and then 38.90 g $Al(OH)_3$ was added hereinto. 1500 ml deionized water was added to the obtained mixture; the mixture was heated up to 60° C. and stirred for 30 minutes. The filter cake obtained by suction filtration was dried overnight at the temperature of 120° C., and then was calcined for 6 hours in a muffle furnace which is heated to the temperature of 650° C. at the heating rate of 10° C./min. The obtained catalyst was pressed and molded to tablets of about 50 mesh, and the tablets were loaded into the micro-reactor for the evaluation of activity.

COMPARATIVE EXAMPLE 5

256.7 g $Cu(NO_3)_2 \cdot 3H_2O$, 60.71 g $Zr(NO_3)_4 \cdot 5H_2O$, 304.83 g $Zn(NO_3)_2 \cdot 6H_2O$ and 176.28 g $Al(NO_3)_3 \cdot 9H_2O$ were dissolved in 1000 ml deionized water to obtain solution A. The precipitator ammonia liquor (with the molar concentration of 4.41 mol/l) was prepared as solution B. 200 ml deionized water was charged into a 2000 ml beaker. Solutions A and B were added simultaneously into another beaker under stirring, the dripping speeds of solutions A and B were controlled, so that the pH value of the solution, was kept at 6.0±0.5. Stirred the system for 1 hour after the titration ended, and then the solution was filtrated by suction and washed for 6 times, the precipitate was collected and dried for 3 hours at the temperature of 120° C., and was calcined for 3 hours at the temperature of 600° C. to obtain the catalyst; the obtained catalyst was pressed and molded to tablets of about 40 mesh, and the tablets were loaded into the micro-reactor for the evaluation of activity.

COMPARATIVE EXAMPLE 6

256.7 g $Cu(NO_3)_2.3H_2O$, 304.83 g $Zn(NO_3)_2.6H_2O$ and 60.71 g $Zr(NO_3)_4.5H_2O$ were dissolved in 1000 ml $H_2O$ to obtain the solution of metal ions, and 200 g $Na_2CO_3$ was dissolved in 2000 ml $H_2O$ to obtain precipitator solution. In water bath of 65° C., the solution of metal ions and the precipitator solution were dropwise added simultaneously for co-precipitation under stirring. The mixture was aged for 1 hour after the dropwise adding ended. The precipitate was washed to remove impurity ions, and then was added by 36.67 g $Al(OH)_3$. Then the obtained mixture was added by 1500 ml deionized water and was heated up to 65° C. and stirred for 30 minutes. The filter cake obtained by suction filtration was dried overnight at the temperature of 120° C., and then was calcined for 3 hours in a muffle furnace which is heated to the temperature of 600° C. at the heating rate of 10° C./min. The obtained catalyst was pressed and molded to tablets of about 50 mesh, and the tablets were loaded into the micro-reactor for the evaluation of activity.

COMPARATIVE EXAMPLE 7

263.34 g $Cu(NO_3)_2.3H_2O$, 57.69 g $Ce(NO_3)_3.6H_2O$, 262.57 g $Zn(NO_3)_2.6H_2O$ and 224.41 g $Al(NO_3)_3.9H_2O$ were dissolved in 1000 ml deionized water to obtain solution A. The precipitator ammonia liquor (with the molar concentration of 4.41 mol/l) was prepared as solution. B. 200 ml deionized water was charged into a 2000 ml beaker, Solutions A and B were added simultaneously into another beaker under stirring, the dripping speed of solutions A and B was controlled, so that the pH value of the solution was kept at 6.5±0.5. The solution was stirred for 1 hour after the titration ended, and then was filtrated by suction and then was washed for 6 times; the precipitate was collected and dried for 3 hours at the temperature of 120° C., and was calcined for 3 hours at the temperature of 600° C. to obtain the catalyst; the obtained catalyst was pressed and molded to tablets of about 40 mesh, and the tablets were loaded into the micro-reactor for the evaluation of activity.

COMPARATIVE EXAMPLE 8

263.34 g $Cu(NO_3)_2.3H_2O$, 235.93 g $Zn(NO_3)_2.6H_2O$ and 57.69 g $Ce(NO_3)_3.6H_2O$ were dissolved in 1000 ml $H_2O$ to obtain solution of metal ions, and 200 g $Na_2CO_3$ was dissolved in 2000 ml $H_2O$ to obtain precipitator solution. In water bath of 70° C., the solution of metal ions and the precipitator solution were dropwise added simultaneously under stirring for co-precipitation. The mixture was aged for 1 hour after the dropwise adding ended. The precipitate was washed to remove impurity ions, and then 46.68 g $Al(OH)_3$ was added hereto. The obtained mixture was added by 1500 ml deionized water, and was heated to 70° C. and stirred for 30 minutes. The filter cake obtained by suction filtration was dried overnight at the temperature of 120° C., and then was calcined for 3 hours in a muffle furnace which is heated to the temperature of 600° C. at the heating rate of 10° C./min. The obtained catalyst was pressed and molded to tablets of about 50 mesh, and the tablets were loaded into the micro-reactor for the evaluation of activity.

Table 1 below lists the physico-chemical properties of the catalysts set forth above. The evaluations of the catalysts in. Tables 3 and 4 were carried out according to the Processing Conditions presented in Table 2, and the evaluations of the catalysts in Table 6 were carried out according to the Processing Conditions presented in Table 5.

TABLE 1

Physico-chemical Properties of the Catalysts

| | Example 1 | Example 2 | Example 3 | Example 4 | Example 5 | Example 6 |
|---|---|---|---|---|---|---|
| Composition, wt % | | | | | | |
| CuO | 37.6 | 32.5 | 45.1 | 55.2 | 60.0 | 39.0 |
| $Al_2O_3$ | 12.3 | 34.0 | 10.4 | 13.0 | 13.5 | 11.0 |
| A, calculated as oxide | 41.6 | 25.0 | 39.0 | 21.4 | 20.0 | 42.0 |
| B, calculated as oxide | 8.5 | 8.5 | 5.5 | 10.4 | 6.5 | 8.0 |
| The content of soluble ion, wt % | | | | | | |
| CuO | 1.50 | 1.40 | 2.01 | 1.75 | 0.77 | 2.21 |
| $Al_2O_3$ | 0.23 | 0.21 | 0.74 | 0.58 | 0.15 | 0.78 |
| Pore size distribution, % | | | | | | |
| 10~30 nm | 82.0 | 80.2 | 79.5 | 81.5 | 85.6 | 80.5 |
| Acid distribution, mmol/g | | | | | | |
| 150~250° C. | 0.047 | 0.040 | 0.057 | 0.055 | 0.036 | 0.062 |
| 250~400° C. | 0.037 | 0.035 | 0.046 | 0.044 | 0.029 | 0.048 |
| 400~500° C. | 0.010 | 0.010 | 0.011 | 0.011 | 0.007 | 0.015 |

| | Example 7 | Example 8 | Example 9 | Example 10 | Example 11 | Example 12 |
|---|---|---|---|---|---|---|
| Composition, wt % | | | | | | |
| CuO | 45.0 | 32.5 | 35.0 | 50.0 | 38.0 | 46.0 |
| $Al_2O_3$ | 15.0 | 30.5 | 14.9 | 14.0 | 13.0 | 20.0 |

TABLE 1-continued

Physico-chemical Properties of the Catalysts

|  |  |  |  |  |  |  |
|---|---|---|---|---|---|---|
| A, calculated as oxide | 30.0 | 25.0 | 41.6 | 23.0 | 40.0 | 23.0 |
| B, calculated as oxide | 10.0 | 12.0 | 8.5 | 13.0 | 9.0 | 11.0 |
| The content of soluble ion, wt % | | | | | | |
| CuO | 0.87 | 1.02 | 1.09 | 1.79 | 1.54 | 2.01 |
| $Al_2O_3$ | 0.28 | 0.30 | 0.38 | 0.65 | 0.35 | 0.55 |
| Pore size distribution, % | | | | | | |
| 10~30 nm | 88.3 | 84.5 | 87.6 | 86.5 | 86.8 | 82.5 |
| Acid distribution, mmol/g | | | | | | |
| 150~250° C. | 0.040 | 0.045 | 0.042 | 0.052 | 0.045 | 0.056 |
| 250~400° C. | 0.035 | 0.038 | 0.040 | 0.046 | 0.042 | 0.048 |
| 400~500° C. | 0.010 | 0.012 | 0.010 | 0.012 | 0.015 | 0.015 |

|  | Example 13 | Example 14 | Example 15 | Example 16 | Example 17 | Example 18 |
|---|---|---|---|---|---|---|
| Composition, wt % | | | | | | |
| CuO | 36.0 | 50.0 | 36.0 | 36.0 | 35.0 | 40.0 |
| $Al_2O_3$ | 11.0 | 13.0 | 18.0 | 16.0 | 15.0 | 14.0 |
| A, calculated as oxide | 43.0 | 27.0 | 36.0 | 39.0 | 39.0 | 36.0 |
| B, calculated as oxide | 10.0 | 10.0 | 10.0 | 9.0 | 11.0 | 10.0 |
| The content of soluble ion, wt % | | | | | | |
| CuO | 1.52 | 1.48 | 2.09 | 1.75 | 0.87 | 2.46 |
| $Al_2O_3$ | 0.68 | 0.51 | 0.78 | 0.55 | 0.45 | 0.68 |
| Pore size distribution, % | | | | | | |
| 10~30 nm | 81.6 | 83.0 | 86.0 | 80.2 | 85.0 | 80.6 |
| Acid distribution, mmol/g | | | | | | |
| 150~250° C. | 0.039 | 0.034 | 0.057 | 0.058 | 0.035 | 0.055 |
| 250~400° C. | 0.034 | 0.032 | 0.048 | 0.046 | 0.029 | 0.045 |
| 400~500° C. | 0.011 | 0.010 | 0.015 | 0.012 | 0.010 | 0.010 |

|  | Example 19 | Example 20 | Example 21 | Example 22 | Example 23 | Example 24 |
|---|---|---|---|---|---|---|
| Composition, wt % | | | | | | |
| CuO | 36.0 | 48.0 | 37.6 | 45.1 | 55.2 | 60.0 |
| $Al_2O_3$ | 14.0 | 15.0 | 12.3 | 10.4 | 13.0 | 13.5 |
| A, calculated as oxide | 41.0 | 25.0 | 41.6 | 39.0 | 21.4 | 20.0 |
| B, calculated as oxide | 9.0 | 12.0 | 8.5 | 5.5 | 10.4 | 6.5 |
| The Content of Soluble Ion, wt % | | | | | | |
| CuO | 1.24 | 1.28 | 1.5 | 2.0 | 1.75 | 0.77 |
| $Al_2O_3$ | 0.19 | 0.16 | 0.23 | 0.74 | 0.58 | 0.15 |
| Pore Size Distribution, % | | | | | | |
| 10 nm~30 nm | 82.0 | 82.6 | 91.5 | 86.7 | 89.6 | 92.4 |
| Acid distribution, mmol/g | | | | | | |
| 150~250° C. | 0.054 | 0.052 | 0.050 | 0.058 | 0.059 | 0.036 |
| 250~400° C. | 0.045 | 0.043 | 0.035 | 0.044 | 0.042 | 0.030 |
| 400~500° C. | 0.013 | 0.016 | 0.009 | 0.010 | 0.012 | 0.006 |

|  | Comparative Example 1 | Comparative Example 2 | Comparative Example 3 | Comparative Example 4 |
|---|---|---|---|---|
| Composition, wt % | | | | |
| CuO | 32.5 | 32.5 | 55.2 | 55.2 |
| $Al_2O_3$ | 34.0 | 34.0 | 13.0 | 13.0 |
| A, calculated as oxide | 25.0 | 25.0 | 21.4 | 21.4 |
| B, calculated as oxide | 8.5 | 8.5 | 10.4 | 10.4 |
| The content of soluble ion, wt % | | | | |
| CuO | 5.34 | 5.67 | 6.30 | 6.34 |
| $Al_2O_3$ | 2.00 | 2.23 | 2.22 | 2.43 |

TABLE 1-continued

Physico-chemical Properties of the Catalysts

Pore size distribution, %

| | | | | |
|---|---|---|---|---|
| 10 nm~30 nm | 74.3 | 72.5 | 70.8 | 71.5 |

Acid distribution, mmol/g

| | | | | |
|---|---|---|---|---|
| 150~250° C. | 0.082 | 0.089 | 0.100 | 0.101 |
| 250~400° C. | 0.072 | 0.075 | 0.090 | 0.092 |
| 400~500° C. | 0.032 | 0.040 | 0.045 | 0.049 |

| | Comparative Example 5 | Comparative Example 6 | Comparative Example 7 | Comparative Example 8 |
|---|---|---|---|---|
| Composition, wt % | | | | |
| CuO | 39.0 | 39.0 | 40.0 | 40.0 |
| $Al_2O_3$ | 11.0 | 11.0 | 14.0 | 14.0 |
| A, calculated as oxide | 42.0 | 42.0 | 36.0 | 36.0 |
| B, calculated as oxide | 8.0 | 8.0 | 10.0 | 10.0 |
| The content of soluble ion, wt % | | | | |
| CuO | 6.45 | 6.78 | 7.34 | 7.17 |
| $Al_2O_3$ | 2.36 | 2.89 | 2.52 | 3.01 |
| Pore size distribution, % | | | | |
| 10 nm~30 nm | 69.7 | 70.8 | 68.5 | 69.3 |
| Acid distribution, mmol/g | | | | |
| 150~250° C. | 0.095 | 0.102 | 0.104 | 0.100 |
| 250~400° C. | 0.082 | 0.085 | 0.095 | 0.090 |
| 400~500° C. | 0.042 | 0.048 | 0.058 | 0.045 |

TABLE 2

Processing Conditions 1

| Raw Materials | Dimethyl Maleate |
|---|---|
| Reaction Temperature/° C. | 190 |
| Liquid Hourly space Velocity/$h^{-1}$ | 0.25 |
| Reaction Pressure/MPa | 6 |
| Hydrogen/ester molar ratio | 200 |

TABLE 3

Evaluation Results of the Activity of the Catalysts

| | | Composition of product, wt % | | |
|---|---|---|---|---|
| Example No. | Conversation ratio, % | 1,4-butanediol | tetrahydrofum | γ-butyrolactone |
| Example 1 | 100 | 85.26 | 2.56 | 9.60 |
| Example 2 | 100 | 84.97 | 3.96 | 9.20 |
| Example 3 | 100 | 84.15 | 2.43 | 8.97 |
| Example 4 | 100 | 85.23 | 2.59 | 4.50 |
| Example 5 | 100 | 86.16 | 2.49 | 4.52 |
| Example 6 | 100 | 85.67 | 5.64 | 7.89 |
| Example 7 | 100 | 86.45 | 2.22 | 9.21 |
| Example 8 | 100 | 86.12 | 3.26 | 9.15 |
| Example 9 | 100 | 85.26 | 3.46 | 8.76 |
| Example 10 | 100 | 84.01 | 6.27 | 8.96 |
| Example 11 | 100 | 84.26 | 7.56 | 7.12 |
| Example 12 | 100 | 86.15 | 6.74 | 5.14 |
| Example 13 | 100 | 86.21 | 3.42 | 6.45 |
| Example 14 | 100 | 85.16 | 3.16 | 8.24 |
| Example 15 | 100 | 83.18 | 7.62 | 4.25 |
| Example 16 | 100 | 82.14 | 7.58 | 4.79 |
| Example 17 | 100 | 65.28 | 3.25 | 5.46 |
| Example 18 | 100 | 83.19 | 2.56 | 7.89 |
| Example 19 | 100 | 84.26 | 7.59 | 5.64 |
| Example 20 | 100 | 83.01 | 7.63 | 6.49 |
| Example 21 | 100 | 85.56 | 2.52 | 9.25 |
| Example 22 | 100 | 84.21 | 2.42 | 8.93 |

TABLE 3-continued

Evaluation Results of the Activity of the Catalysts

| | | Composition of product, wt % | | |
|---|---|---|---|---|
| Example No. | Conversation ratio, % | 1,4-butanediol | tetrahydrofum | γ-butyrolactone |
| Example 23 | 100 | 85.23 | 2.47 | 4.21 |
| Example 24 | 100 | 87.23 | 2.46 | 4.48 |
| Comparative Example 1 | 100 | 66.59 | 5.79 | 6.25 |
| Comparative Example 2 | 100 | 65.48 | 3.55 | 6.96 |
| Comparative Example 3 | 99.8 | 66.79 | 4.22 | 6.85 |
| Comparative Example 4 | 98.7 | 68.46 | 5.16 | 7.49 |
| Comparative Example 5 | 98.5 | 69.45 | 5.46 | 8.32 |
| Comparative Example 6 | 97.8 | 70.45 | 5.62 | 8.24 |
| Comparative Example 7 | 96.8 | 72.46 | 5.89 | 9.21 |
| Comparative Example 8 | 97.2 | 73.24 | 6.02 | 8.76 |

TABLE 4

Results of the Stability Test of the Catalysts (the test time was 500 hours)

| | | Composition of product | | |
|---|---|---|---|---|
| | Conversion ratio, % | 1,4-butanediol | tetrahydrofuran | γ-butyrolactone |
| Example 2 | 100 | 84.75 | 3.86 | 8.89 |
| Example 6 | 100 | 85.42 | 5.48 | 7.58 |
| Comparative Example 1 | 100 | 64.21 | 5.46 | 6.75 |

TABLE 4-continued

Results of the Stability Test of the Catalysts
(the test time was 500 hours)

| | Conversion ratio, % | Composition of product | | |
| --- | --- | --- | --- | --- |
| | | 1,4-butanediol | tetrahydrofuran | γ-butyrolactone |
| Comparative Example 2 | 100 | 63.19 | 3.12 | 7.00 |

Notes: the conversion ratio and the composition, of product in the table are expressed in percent by weight, and the conversion ratio was calculated by dimethyl succinate. The composition of product in the table was calculated on the basis of the sum of 10 reaction products being 100%, the 10 reaction, products are: 1,4-butanediol tetrahydrofuran, γ-butyrolaetone, hydroxybutyraldehyde, hydroxytetrahydrofuran, n-butanol, methyl hydroxybutyrate, 2-(4-hydroxybutoxy)tetrahydrofuran, 4,4'-dihydroxydibuthyl ester and dimethyl succinate.

TABLE 5

Processing Conditions 2

| Raw Materials | dimethyl maleate |
| --- | --- |
| Reaction Temperature/° C. | 195 |
| Liquid Hourly space Velocity/h$^{-1}$ | 0.25 |
| Reaction Pressure/MPa | 6 |
| Hydrogen/Ester molar ratio | 200 |

TABLE 6

Evaluation Results of the Activity of the Catalyst

| Example No. | Conversion ratio, % | Composition of product, wt % | | |
| --- | --- | --- | --- | --- |
| | | 1,4-butanediol | tetrahydrofuran | γ-butyrolactone |
| Example 2 | 100 | 83.56 | 4.97 | 10.02 |
| Example 18 | 100 | 81.56 | 4.85 | 9.68 |
| Example 21 | 100 | 83.56 | 4.78 | 10.15 |
| Comparative Example 1 | 100 | 63.25 | 7.87 | 7.96 |
| Comparative Example 2 | 100 | 63.59 | 4.79 | 8.41 |
| Comparative Example 7 | 100 | 70.12 | 7.52 | 9.87 |
| Comparative Example 8 | 100 | 70.59 | 8.06 | 9.07 |

Notes: the conversion ratio and she composition of product in the table are expressed, in percent by weight; and the conversion, ratio was calculated by dimethyl succinate. The composition of product in the table was calculated on the basis of the sum of 10 reaction, products being 100%, the 10 reaction products are; 1,4-butanediol, tetrahydrofuran, γ-butyrolactone, hydroxybutyraldehyde, hydroxytetrahydrofuran, n-butanol, methyl hydroxybutyrate, 2-(4-hydyoxybutoxy)tetrahydrofuran, 4,4'-dihydroxydibuthyl ester and dimethyl succinate.

What is claimed is:

1. A hydrogenation catalyst comprising Cu—Al-A-B—O, wherein A comprises at least one of Zn, Mo and W, and B comprises at least one of Ba, Mn, Mg, Ti, Ce and Zr; further wherein;

the amount of copper oxide ranges from about 30% to about 70% by weight relative to the total weight of the catalyst, the amount of aluminum oxide ranges from about 10% to about 40% by weight relative to the total weight of the catalyst, the content of A calculated as oxide ranges from about 20% to about 50% by weight relative to the total weight of the catalyst, the content of B calculated as oxide ranges from about 5% to about 15% by weight relative to the total weight of the catalyst, and the acid distribution measured by ammonia adsorption-TPD method comprises: the amount of acid sites at the temperature of 150~250° C. ranges from about 0.025 mmol/g to about 0.070 mmol/g, the amount of acid sites at the temperature of 250~400° C. ranges from about 0.020 mmol/g to about 0.065 mmol/g, the amount of acid sites at the temperature of 400~500° C. ranges from about 0.005 mmol/g to about 0.020 mmol/g.

2. The hydrogenation catalyst according to claim 1, wherein the total amount of soluble active metal ion of copper and aluminum, calculated as oxide, ranges from about 0.5% to about 4.0% by weight relative to the total weight of the catalyst.

3. The hydrogenation catalyst according to claim 1, wherein the specific surface area of said hydrogenation catalyst ranges from about 25 m$^2$/g to about 50 m$^2$/g, the pore volume of said hydrogenation catalyst ranges from about 0.10 ml/g to about 0.25 ml/g, and average pore diameter of said hydrogenation catalyst ranges from about 14 nm to about 25 nm.

4. The hydrogenation catalyst according to claim 1, comprising pores with a diameter ranging from about 10 nm to about 30 nm in an amount ranging from about 75% to about 95% by volume relative to the total pore volume of the catalyst.

5. The hydrogenation catalyst, according to claim 4, comprising pores with a diameter of ranging from about 10 nm to about 30 nm in an amount ranging from about 80% to about 95% by volume relative to the total pore volume of the catalyst.

6. A process for producing 1,4-butanediol comprising hydrogenating dialkyl maleate and/or dialkyl succinate with the hydrogenation catalyst of claim 1.

7. The process according to claim 6, wherein the carbon atom number of the alkyl of said dialkyl maleate and/or dialkyl succinate ranges from 1 to 4.

8. The process according to claim 6, wherein the dialkyl maleate is chosen from at least one of dimethyl maleate, diethyl maleate, and dibutyl maleate.

9. The process according to claim 6, wherein the dialkyl succinate is chosen from at least one of dimethyl succinate, diethyl succinate, and dibutyl succinate.

10. The process according to claim 6, wherein the conditions for hydrogenating dialkyl maleate and/or dialkyl succinate comprise; a reaction pressure ranging front about 4 MPa to about 8 MPa, a reaction temperature ranging from about 160° C. to about 240° C., the molar ratio of hydrogen to ester ranges from about 100:1 to about 400:1, and the liquid hourly space velocity of the dialkyl maleate and/or the dialkyl succinate ranges from about 0.1 h$^{-1}$ to about 2.0 h$^{-1}$.

11. The process according to claim 10, wherein the condition for hydrogenating dialkyl maleate and/or dialkyl succinate comprises: a reaction pressure ranging from about 5 MPa to about 6 MPa, a reaction temperature ranging from about 180° C. to about 200° C., the molar ratio of hydrogen to ester ranges from about 200:1 to about 300:1, and the liquid hourly space velocity of the dialkyl maleate and/or the dialkyl succinate ranges from about 0.2 h$^{-1}$ to about 0.5 h$^{-1}$.

12. A process for preparing a hydrogenation catalyst comprising:
(1) preparing a first mixed solution comprising soluble salts of Cu and A, wherein A comprises at least one of Zn, Mo and W; dropwise adding simultaneously the first mixed solution and a precipitator I under stirring to form a precipitation system, and controlling the pH value of the precipitation system to be ranging from about 4.0 to about 6.5, wherein the temperature of the precipitation system ranges from about 15° C. to about 40° C.; wherein the amount of Cu used in step (1) ranges from about 45 wt % to about 55 wt % of the total used amount of Cu, and the rest of Cu is introduced m step (2);
(2) preparing a second mixed solution comprising Cu, Al and B, wherein B comprises at least one of Ba, Mn, Mg, Ti, Ce and Zr; dropwise adding simultaneously the second mixed solution and a precipitator II to the precipitation system obtained in step (1) under stirring, increasing the temperature of the precipitation system to range from about 45° C. to about 80° C., and controlling the pH value of the precipitation system range from about 5.5 to about 8.5;
(3) drying the precipitation system obtained in step (2) at a drying temperature ranging from about 100° C. to about 200° C., and then calcining for a period of time ranging from about 2 hours to about 8 hours at a temperature ranging from about 500° C. to about 900° C. to obtain the hydrogenation catalyst.

13. The process according to claim 12, wherein in the step (1), the total concentration of the metal ions of Cu and A ranges from about 0.5 mol/l to about 3.5 mol/l, and the concentration of the precipitator I ranges from about 3.0 mol/l to about 6.0 mol/l.

14. The process according to claim 13, wherein in the step (1), the total concentration of the metal ions of Cu and A ranges from about 0.8 mol/l to about 3.0 mol/l.

15. The process according to claim 12, wherein in the step (2), the total concentration of the metal ions of Cu, Al and B ranges from about 0.5 mol/l to about 3.5 mol/l, and the concentration of the precipitator II ranges from about 1.0 mol/l to about 2.0 mol/l.

16. The process according to claim 15, wherein in the step (2), the total concentration of the metal ions of Cu, Al and B ranges from about 0.8 mol/l to about 2.0 mol/l.

17. The process according to claim 12, wherein said soluble salts of Co, Al, A and B are chosen from at least one of nitrates and acetates salts thereof; and when A is W, the soluble salt thereof is ammonium metatungstate; and the precipitator I comprises at least one of ammonium bicarbonate, ammonium carbonate, and ammonia liquor; the precipitator II comprises at least one of ammonium bicarbonate, ammonium carbonate, and ammonia liquor.

18. The process according to claim 12, wherein in the step (3), the drying temperature ranging from about 100° C. to about 200° C. is obtained at the heating rate of 10° C./min.

19. The process according to claim 12, wherein in the step (1), stirring the system at constant temperature for a period of time ranging from about 30 minutes to about 90 minutes after the dropwise adding ends.

20. The process according to claim 12, wherein in the step (1), stirring the system at constant temperature for a period ranging from about 80 minutes to about 120 minutes after the dropwise adding ends.

21. The process according to claim 12, wherein in the step (3), the calcining temperature ranges from about 600° C. to about 850° C.

22. The process according to claim 12, wherein the step (2) comprising adding at least one polyether type nonionic surfactant in an amount ranging from about 0.05% to about 2.0% by volume relative to the total volume of the materials obtained in the step (2).

23. The process according to claim 22, wherein said polyether type nonionic surfactant is added to the second mixed solution of the soluble salts of Cu, Al and B, is added to the precipitator II, or is added to the precipitation system.

24. The process according to claim 22, wherein said polyether type nonionic surfactant comprises at least one surfactant chosen from RPE-type nonionic surfactants and PEP-type nonionic surfactants.

25. The process according to claim 22, wherein said polyether type nonionic surfactant comprises at least one surfactant chosen from polyoxyethylene polyoxypropylene pentaerythritol ether, polyoxyethylene polyoxypropylene ether, polyoxypropylene glycerol ether and polyoxypropylene oxyethylene glycerol ether.

* * * * *

UNITED STATES PATENT AND TRADEMARK OFFICE
CERTIFICATE OF CORRECTION

PATENT NO.        : 9,168,509 B2
APPLICATION NO.   : 13/663733
DATED             : October 27, 2015
INVENTOR(S)       : Yanxia Zhang et al.

Page 1 of 1

It is certified that error appears in the above-identified patent and that said Letters Patent is hereby corrected as shown below:

Title page, item (73), lines 2-4, "Fushun Research Institute of Petroleum, Fushun, Liaoning Province (CN)" should read --Fushun Research Institute of Petroleum and Petrochemicals, Sinopec, Fushun City, Liaoning Province (CN)--.

In the Claims:

Claim 10, col. 24, line 57, "ranging front" should read --ranging from--.

Signed and Sealed this
Second Day of August, 2016

Michelle K. Lee
*Director of the United States Patent and Trademark Office*